United States Patent [19]

Bouillon et al.

[11] 4,275,199

[45] Jun. 23, 1981

[54] PROCESS FOR PREPARING MIXED SULFONATES OF BIS-(N-OXYPYRIDYL-2-THIO)ALUMINUM

[75] Inventors: Claude Bouillon, Eaubonne; Georges Rosenbaum, Asnieres, both of France

[73] Assignee: L'Oreal, Paris, France

[21] Appl. No.: 110,499

[22] Filed: Jan. 8, 1980

Related U.S. Application Data

[63] Continuation of Ser. No. 925,882, Jul. 18, 1978, abandoned.

[30] Foreign Application Priority Data

Jul. 21, 1977 [FR] France .................. 77 22391

[51] Int. Cl.³ .................................. C07D 213/89
[52] U.S. Cl. .............................. 542/430; 546/6; 260/448 AD; 424/68; 424/258; 424/263
[58] Field of Search ........................ 546/6

[56] References Cited

U.S. PATENT DOCUMENTS

| | | | |
|---|---|---|---|
| 3,953,450 | 4/1976 | Bouillon et al. | 546/6 |
| 4,072,742 | 2/1978 | Bouillon et al. | 424/47 |

FOREIGN PATENT DOCUMENTS 2183647 12/1973 France .
2236515 2/1975 France .
2282426 3/1976 France .

*Primary Examiner*—Mark L. Berch
*Attorney, Agent, or Firm*—Cushman, Darby & Cushman

[57] ABSTRACT

A process is disclosed for the preparation of bis-(N-oxypyridyl-thio) derivatives of aluminum sulfonates by reacting a bis-isopropylate aluminum derivative of an organic sulfonate with two equivalents of the N-oxide of pyridine-2 thiol. The bis-isopropylate aluminum derivative of the organic sulfonate is formed by reacting the organic sulfonic acid precursor with aluminum isopropylate.

6 Claims, No Drawings

PROCESS FOR PREPARING MIXED SULFONATES OF BIS-(N-OXYPYRIDYL-2-THIO)ALUMINUM

This is a continuation of application Ser. No. 925,882 filed July 18, 1978, abandoned.

The present invention is directed to a new process for the preparation of mixed organic salts of aluminum, and more particularly to sulfonates of bis-(N-oxypyridyl-2 thio)aluminum.

The compounds of the invention can be represented by the following general formula:

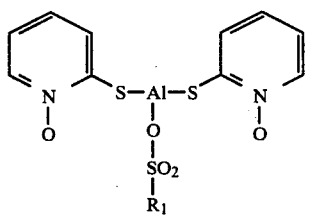

in which:
$R_1$ represents a radical selected from the group consisting of
(i) an alkyl having 1 to 4 carbon atoms,
(ii) a radical of the formula

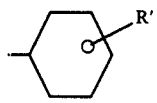

in which R' represents methyl, chloro or hydroxy,
(iii) a radical of the formula:

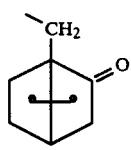

(iv) a radical of the formula:

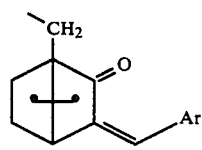

in which Ar is $C_6H_5$— or p—$CH_3$ $C_6H_4$—,
(v) a radical of the formula:

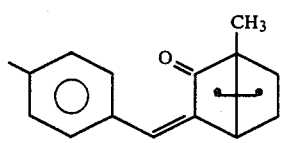

(vi) a radical of the formula:

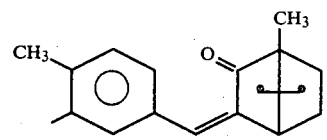

(vii) a radical of the formula:

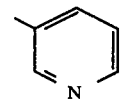

(viii) a radical of the formula:

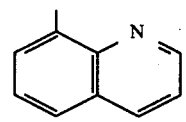

(ix) a radical of the formula:

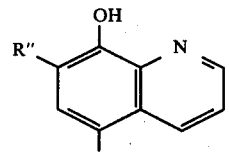

in which R" is hydrogen or iodo,
(x) —$CH_2$—$CH_2$—$NH_2$, and
(xi) —$CH_2$—CH (COOH)—$NH_2$.

A process for the preparation of compounds of the foregoing type, particularly those in which $R_1$ is alkyl of 1 to 4 carbon atoms, phenyl, parachlorophenyl, parahydroxyphenyl or oxo-2 bornanyl-10, has been proposed.

This process is described in French Pat. No. 2183647 and can be represented by Equation A which follows:

EQUATION A

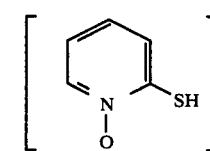

(1)
+
Al [OCH—$(CH_3)_2]_3$
(2)

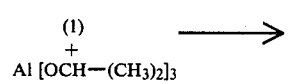

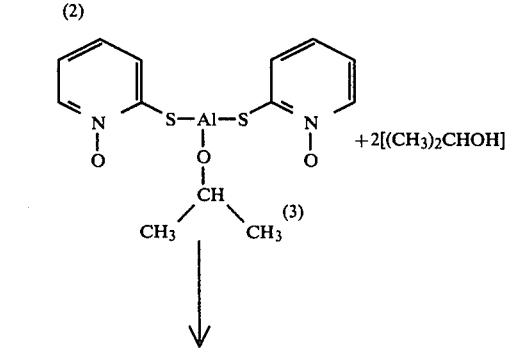

-continued

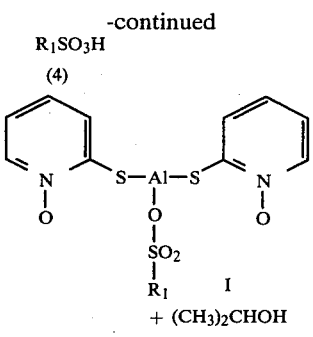

+ (CH$_3$)$_2$CHOH

This process comprises first preparing an intermediate compound (3) by a reaction between aluminum isopropylate (2) with the N-oxide of pyridine-2 thiol (1) in an anhydrous solvent at ambient or at elevated temperature.

The intermediate compound (3) is suspended in an anhydrous solvent and treated with a sulfonic acid (4) to form the compound of formula (I).

The solvents which may be used in the reaction to produce compounds of formula (I) include alcohols, aromatic hydrocarbons and chlorinated hydrocarbons, notably chloroform.

Although said process permits the production of compounds of formula (I) in good yields, it presents certain difficulties, notably, the products obtained are extremely difficult to dry. This is probably due to the fact that the reaction continues to follow its course with the progressive elimination of isopropanol.

Consequently, it is practically impossible to attain products of constant weight.

The new process according to the invention can be represented by Equation B which follows:

EQUATION B

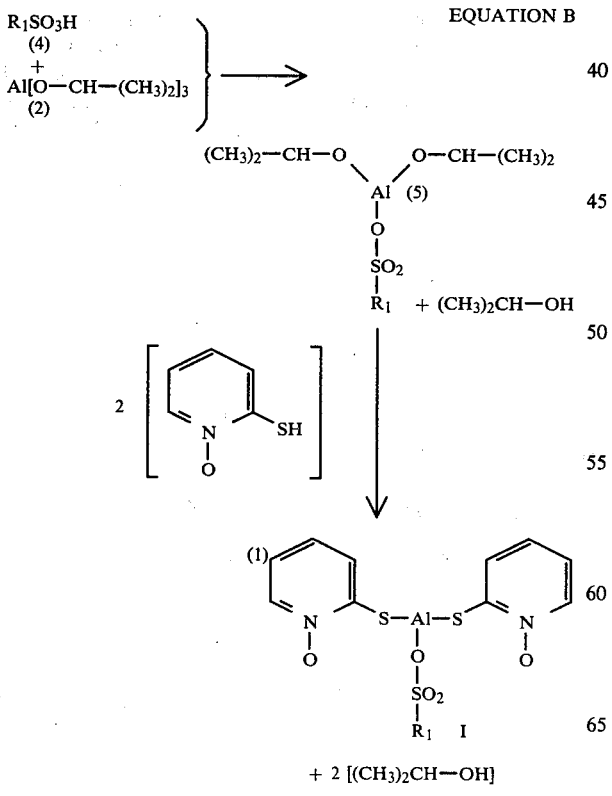

The new process according to the invention comprises in a first stage preparing the intermediate compound (5) by reacting an equimolar quantity of aluminum isopropylate (2) with the sulfonic acid R$_1$SO$_3$H (4) in an anhydrous solvent, and then in a second stage reacting said intermediate compound with two equivalents of the N-oxide of pyridine-2 thiol dissolved in a solvent which is identical or different from that used to conduct the reaction in the first stage.

The reaction is generally effectuated at a temperature equal to or greater than 20° C. and preferably at the reflux temperature of the solvent or the mixture of solvents in which the reaction is conducted.

After the reaction, the product is isolated by concentration to dryness under reduced pressure.

The anhydrous solvents which may be principally employed according to the process of the invention are selected from the group consisting of chlorinated solvents such as chloroform or dichloroethane, an aromatic solvent such as benzene or toluene or possibly an alcohol such as isopropanol.

The intermediate compound (5) can be, if desired, isolated before undertaking the second stage of the process of the invention. However, as a practical matter, for obtaining a good yield of final product, the intermediate (5) is not preferably isolated from its reaction mixture.

The present process of the invention, as compared to that described in French Pat. No. 2183647 has the advantage of permitting more complete reaction in a much shorter period of time. In addition, the process of the invention offers greater certainty of complete reaction at each stage of the synthesis. Moreover, the period of time required for drying the ultimate product is considerably reduced and an improved quality of final product is an inevitable result.

Apparently, in the process of the invention, the strong acidity of the sulfonic acid R$_1$—SO$_3$H (4) permits a more rapid displacement of the isopropoxy radical than does the action of the N-oxide of pyridine-2 thiol (1) which is in equilibrium with a tautomer form identified as N-hydroxydihydropyridinethione-2. The displacement of the two isopropoxy radicals of the intermediate compound (5), by the N-oxide of pyridine-2 thiol to form the compound of formula (I), is favored in the presence of a catalyst of an acid nature (in the sense of a Lewis acid).

The sulfonic acids R$_1$SO$_3$H, R$_1$ being defined as above, are for the most part known compounds, the preparations of which have been described in the literature. In particular, the sulfonic acids derived from camphor have been described in French Pat. Nos. 2236515 and 2282426.

Among the compounds which can be obtained in accordance with the invention are the following:

(1) the campho-10 sulfonate of bis-(N-oxypyridyl-2 thio)aluminum,
(2) the p-toluenesulfonate of bis-(N-oxypyridyl-2 thio)aluminum,
(3) the p-hydroxybenzenesulfonate of bis-(N-oxypyridyl-2 thio)aluminum,
(4) the methanesulfonate of bis-(N-oxypyridyl-2 thio)aluminum,
(5) the p-chlorobenzenesulfonate of bis-(N-oxypridyl-2 thio)aluminum,
(6) the benzene sulfonate of bis-(N-oxypyridyl-2 thio)aluminum, (7) the oxo-2 bornylidene-3 methyl)-4 benzene sulfonate of bis-(N-oxypyridyl-2 thio)aluminum, (8) the methyl-2(oxo-2 bornylidene-3 methyl)-5 benzene sulfonate of bis-(N-oxypyridyl-2 thio)aluminum, (9) the benzylidene-3 campho-10 sulfonate of bis-(N-oxypyridyl-2 thio)aluminum,

(10) the tolylidene-3 campho-10 sulfonate of bis-(N-oxypyridyl-2 thio)aluminum,

(11) the pyridine-3 sulfonate of bis-(N-oxypyridyl-2 thio)aluminum,

(12) the quinoline-8 sulfonate of bis-(N-oxypyridyl-2 thio)aluminum,

(13) the hydroxy-8 quinoline-5 sulfonate of bis-(N-oxypyridyl-2 thio)aluminum,

(14) the hydroxy-8 iodo-7 quinoline-5 sulfonate of bis-(N-oxypyridyl-2 thio)aluminum,

(15) the β-amino ethane sulfonate of bis-(N-oxypyridyl-2 thio)aluminum, and

(16) the amino-2 carboxy-2 ethane sulfonate of bis-(N-oxypyridyl-2 thio)aluminum.

The present invention is also directed to new industrial compounds having the following general formula:

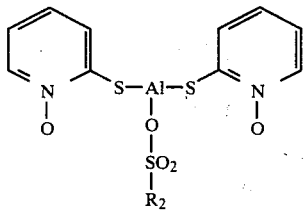

II in which
R$_2$ represents a radical selected from the group consisting of
(i) a radical of the formula:

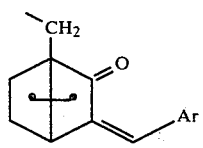

in which Ar is C$_6$H$_5$ or p—CH$_3$C$_6$H$_4$—
(ii) a radical of the formula:

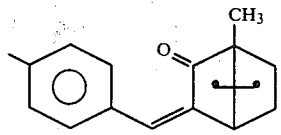

(iii) a radical of the formula:

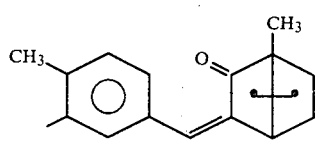

(iv) a radical of the formula:

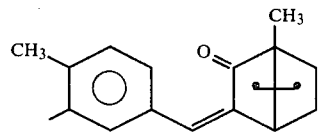

(v) a radical of the formula:

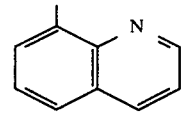

(vi) a radical of the formula:

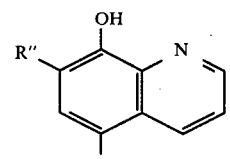

in which R″ represents hydrogen or iodo
(vii) —CH$_2$—CH$_2$—NH$_2$, and
(viii) —CH$_2$—CH(COOH)—NH$_2$.

Among the new compounds corresponding to formula (II) compounds 7 through 16 enumerated above can be noted.

The new compounds present an excellent antimicrobial activity against diverse types of micro-organisms including notably, *Micrococcus Aureus, Bacillus Subtilis, Sarcina Lutea, Escherichia Coli, Aspergillus Niger, penicillium Notatum, Mucor Mucedo, Saccharomyses Cerevisiae, Pityrosporum Ovale* and *Candida Albicans.*

Among the particular properties of these compounds is their utility in cosmetics for realizing deodorant compositions, antiperspirants, anti-pellicular, for feminine hygiene.

The following examples, presented by way of illustration of the invention, are not to be considered limiting but exemplary of the process according to the invention.

EXAMPLES

Example A

Preparation of the (oxo-2 bornylidene-3 methyl)-4 benzene sulfonate of bis-N(oxypyridyl-2 thio)-aluminum (compound 7).

A mixture of 4.08 g of aluminum isopropylate and 6.4 g of (oxo-2 bornylidene-3 methyl)-4 benzene sulfonic acid in 50 milliliters of benzene are heated to reflux for a period of one hour.

To the resulting solution are added 5.08 g of N-oxide of pyridine-2 thiol in 25 milliliters of benzene, and the mixture is heated to the boiling point for a period of time of two hours. Then the reaction mixture is concentrated to dryness under reduced pressure. 11.56 g of a whitish powder are recovered, for which the corresponding analysis has been determined:

Calc.: % Al 4.51, S 16.05: Found: % Al 4.70, S 15.65.

Example B

Preparation of campho-10 sulfonate of bis-(N-oxypyridyl-2 thio)aluminum (compound 1).

A mixture of 4.8 g of campho-10 sulfonic acid and of 4.08 g of aluminum isopropylate in 50 milliliters of dichloroethane is heated for an hour at gentle reflux. Then, a solution of 5.8 g of the N-oxide of pyridine-2 thiol in 30 milliliters of dichloroethane was introduced, and then the mixture was heated to boiling for two hours. The solution is concentrated to dryness under reduced pressure. A white product (10.5 g) was obtained, in which the characteristic analysis was determined:

Calc.: % Al 5.29, S 18.82: Found: % Al 5.30, S 18.95.

The same result is obtained when dichloroethane was replaced by isopropanol.

According to the same mode of operation, described in Examples A and B above, the following compounds were prepared:

| Ex. | Compound | Weight Obtained (g)* | Al % Calc. | Al % Found | S % Calc. | S % Found |
|---|---|---|---|---|---|---|
| C | Compound 2 | 9.2 | 6.0 | 6.11 | 21.33 | 21.13 |
| D | Compound 11 | 9.2 | 6.18 | 5.99 | 21.96 | 21.58 |
| E | Compound 12 | 9.8 | 5.54 | 5.49 | 19.69 | 19.04 |
| F | Compound 13 | 10.2 | 5.37 | 5.32 | 19.09 | 18.86 |
| G | Compound 14 | 13.2 | 4.29 | 4.34 | 15.25 | 14.51 |

*Based on 20 millimoles of the sulfonic acid.

Example H

Preparation of β-amino-2 ethane sulfonate of bis-(N-oxypyridyl-2 thio)aluminum (compound 15).

10.2 g (50 millimoles) of aluminum isopropylate were dissolved in 100 milliliters of isopropanol. 6.25 g of taurine was added and then heating (to reflux) were continued for one hour.

A solution of 12.7 g (100 millimoles) of N-oxide of pyridine-2 thiol in 50 milliliters of isopropanol was introduced and the mixture was heated at reflux temperature for two hours. Then, the reaction mixture was concentrated to dryness. A white powder was recovered; the weight and characteristic analysis of the product was determined:

Product yield: 20.4 g (theoretical 50 millimoles: 20.15 g).

Calc.: % Al 6.75: Found: % Al 6.70.

Example I

Preparation of the amino-2 carboxy-2 ethanesulfonate of bis-(N-oxypyridyl-2 thio)aluminum (compound 16)

The same method of preparation, as described in Example H was applied to the preparation of this compound, by replacing the taurine by cysteic acid (8.45 g).

A white product was recovered.

The yield of product was 22.55 g (theory 50 millimoles: 22.35 g).

Analysis: Calc.: % Al 5.93: Found: % Al 6.04.

What is claimed is:

1. Process for preparing compounds of the formula:

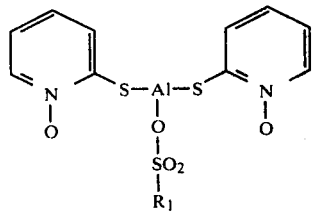

in which $R_1$ is selected from the group consisting of (i) alkyl of 1 to 4 carbon atoms, (ii)

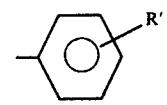

in which R' is methyl, chloro or hydroxy,

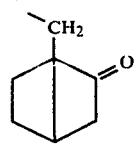 (iii)

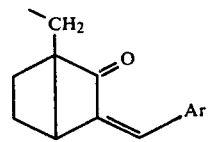 (iv)

in which Ar is $C_6H_5$— or p—$CH_3C_6H_4$—,

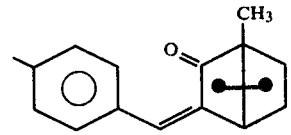 (v)

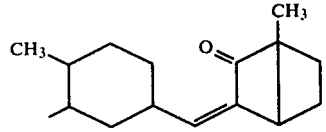 (vi)

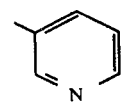 (vii)

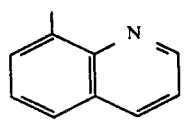 (viii)

-continued

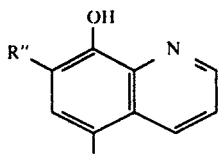

in which R" is hydrogen or iodo;

(x) —CH$_2$—CH$_2$—NH$_2$, and (xi) —CH$_2$—CH(COOH)—NH$_2$ wherein said process is undertaken in two stages; wherein in a first stage an intermediate compound of the formula

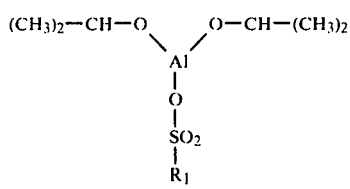

is prepared by reacting an equimolar quantity of aluminum isopropylate with a sulfonic acid of the formula R$_1$SO$_3$H wherein R$_1$ is as defined above and wherein in a second stage, said intermediate compound is reacted with two equivalents of the N-oxide of pyridine-2 thiol.

2. The process according to claim 1, wherein said first and second stages are undertaken in an anhydrous solvent or in a mixture of anhydrous solvents.

3. The process according to claim 2, wherein said solvent is selected from the group consisting of chloroform, dichloroethane, benzene, toluene and isopropanol.

4. The process according to claim 1 wherein said stages are undertaken at a temperature of at least 20° C.

5. The process according to claim 1, wherein said stages are undertaken at the boiling point of the solvent or mixture of solvents.

6. The process according to claim 2, wherein the product obtained is isolated by concentrating under reduced pressure.

* * * * *

UNITED STATES PATENT AND TRADEMARK OFFICE
CERTIFICATE OF CORRECTION

PATENT NO. : 4,275,199
DATED : June 23, 1981
INVENTOR(S) : Claude BOUILLON and Georges ROSENBAUM It is certified that error appears in the above-identified patent and that said Letters Patent are hereby corrected as shown below:

Column 1, between lines 31 and 38, the structural formula should read:

Column 2, line 65, should read

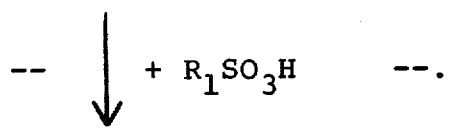

Column 3, line 2, delete -- $R_1SO_3H$ --.

Column 3, between lines 50 and 55, the structural formula should read:

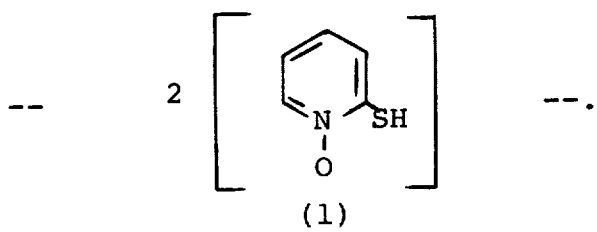

UNITED STATES PATENT AND TRADEMARK OFFICE
CERTIFICATE OF CORRECTION

PATENT NO. : 4,275,199
DATED : June 23, 1981
INVENTOR(S) : Claude Bouillon and Georges Rosenbaum It is certified that error appears in the above—identified patent and that said Letters Patent is hereby corrected as shown below:

Column 3, between lines 57 and 65, the structural formula should read:

-- 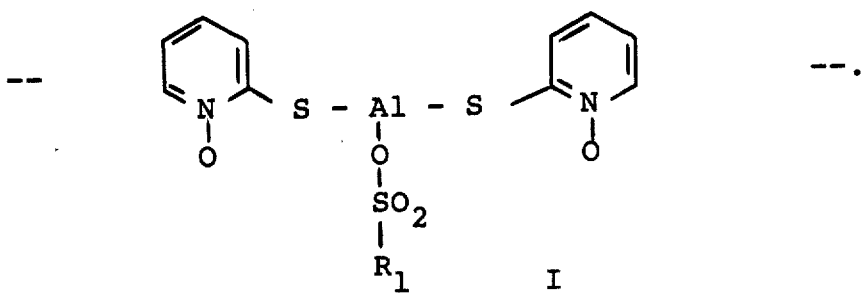 --.

Column 6, between lines 1 and 8, the structural formula should read:

-- 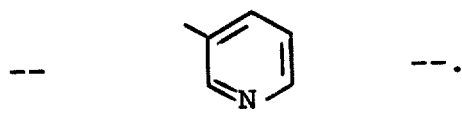 --.

UNITED STATES PATENT AND TRADEMARK OFFICE
CERTIFICATE OF CORRECTION

PATENT NO. : 4,275,199            Page 3 of 4
DATED : June 23, 1981
INVENTOR(S) : Claude Bouillon and Georges Rosenbaum It is certified that error appears in the above—identified patent and that said Letters Patent is hereby corrected as shown below:

Column 8, between lines 27 and 32, the structural formula should read:

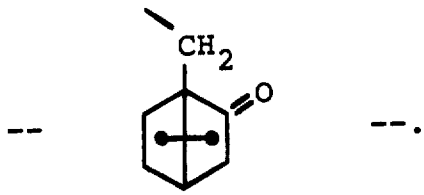

Column 8, between lines 35 and 40, the structural formula should read:

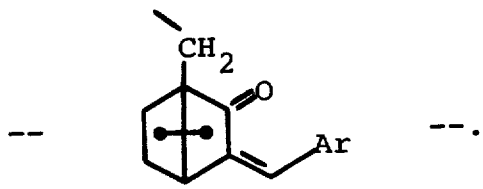

UNITED STATES PATENT AND TRADEMARK OFFICE
CERTIFICATE OF CORRECTION

PATENT NO. : 4,275,199

DATED : June 23, 1981

INVENTOR(S) : Claude Bouillon and Georges Rosenbaum

It is certified that error appears in the above—identified patent and that said Letters Patent is hereby corrected as shown below:

Column 8, between lines 50 and 55, the structural formula should read:

-- 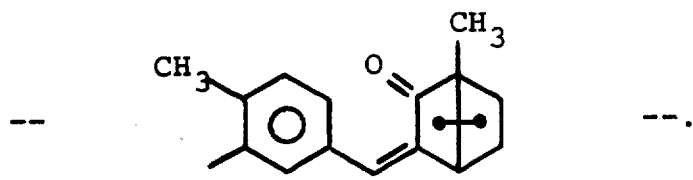 --.

Signed and Sealed this

Twelfth Day of January 1982

[SEAL]

Attest:

Attesting Officer

GERALD J. MOSSINGHOFF

Commissioner of Patents and Trademarks